US006803058B1

United States Patent
Tuxford et al.

(10) Patent No.: US 6,803,058 B1
(45) Date of Patent: Oct. 12, 2004

(54) FOOT POWDERS AND METHODS FOR THEIR USE

(76) Inventors: George M. Tuxford, 2873 Europa Dr., Costa Mesa, CA (US) 92626; Jack E. Tuxford, 176 Center Street, London, Ontario (CA)

( * ) Notice: Subject to any disclaimer, the term of this patent is extended or adjusted under 35 U.S.C. 154(b) by 0 days.

(21) Appl. No.: 10/623,049

(22) Filed: Jul. 18, 2003

(51) Int. Cl.$^7$ .......................... A01N 59/14; A61K 33/22
(52) U.S. Cl. ....................................... 424/659; 424/703
(58) Field of Search ............................ 514/64; 424/659, 424/703

(56) References Cited

U.S. PATENT DOCUMENTS

| | | | |
|---|---|---|---|
| 67,921 A | | 8/1867 | Spear |
| 168,219 A | | 9/1875 | Bowen |
| 321,839 A | | 7/1885 | Neuer |
| 1,029,203 A | * | 6/1912 | Loewenthal ................ 424/658 |
| 1,783,695 A | * | 12/1930 | Blumenberg, Jr. .......... 424/659 |
| 2,095,571 A | | 10/1937 | Nichols |
| 2,102,564 A | | 12/1937 | Bonstein |
| 2,210,013 A | | 8/1940 | Teller |
| 2,289,125 A | | 7/1942 | Keil |
| 3,267,091 A | | 8/1966 | Denison |
| 4,428,933 A | | 1/1984 | King |
| 4,954,334 A | * | 9/1990 | Pugh et al. ................... 424/68 |
| 5,258,183 A | | 11/1993 | Grimberg |

\* cited by examiner

*Primary Examiner*—Alton N. Pryor
(74) *Attorney, Agent, or Firm*—Eric K. Satermo

(57) ABSTRACT

A foot powder includes boric acid powder and sublimed sulfur powder. In a number of embodiments, the foot powder includes about 40% to about 60% by weight of boric acid powder and about 40% to about 60% by weight of sublimed sulfur powder. In other embodiments, the ratio of boric acid powder to sublimed sulfur powder is about 1:1, that is, about 50% by weight of boric acid powder and about 50% by weight of sublimed sulfur powder. The foot powder may be used to treat foot odor and wetness.

9 Claims, No Drawings

FOOT POWDERS AND METHODS FOR THEIR USE

BACKGROUND OF THE INVENTION

The present invention relates to topical foot powders suitable for use on mammalian skin.

Conventional foot powders use a variety of ingredients to provide a desired effect, such as cooling, heating, and preventing perspiration or odor. Ingredients of such compositions have generally included inorganic compounds of aluminum, zinc, and zirconium having an astringent effect upon the skin; substances which prevent irritation of the skin; and anti-microbial compounds. In addition, fragrances and other ingredients may be added.

BRIEF SUMMARY OF THE INVENTION

According to one aspect of the invention, a foot powder includes boric acid powder and sublimed sulfur powder. In a number of embodiments, the foot powder includes about 40% to about 60% by weight of boric acid powder and about 40% to about 60% by weight of sublimed sulfur powder. In other embodiments, the ratio of boric acid powder to sublimed sulfur powder is about 1:1, that is, about 50% by weight of boric acid powder and about 50% by weight of sublimed sulfur powder. The foot powder may be used to treat foot odor and wetness.

According to another aspect, a foot powder includes only boric acid powder and sublimed sulfur powder, for example, at a ratio of about 1:1. These embodiments enjoy the benefit of ease of production and low cost. In addition, the risk of allergic reaction that may have occurred with additional ingredients is eliminated.

Other features and advantages of the present invention will become apparent to those skilled in the art from a consideration of the following detailed description taken in conjunction with the accompanying drawings.

DETAILED DESCRIPTION OF THE INVENTION

The foot powders of the present invention are capable of reducing or eliminating foot odor and wetness. The components of these compositions are described below. The present invention can comprise, consist of, or consist essentially of any of the required or optional ingredients and/or limitations described herein. All percentages and ratios are calculated on a weight basis unless otherwise indicated. All percentages are calculated based upon the total composition unless otherwise indicated. All ingredient levels are exclusive of solvents, by-products, or other impurities that may be present in commercially available sources, unless otherwise indicated. All documents referred to herein, including patents, patent applications, and printed publications, are hereby incorporated by reference in their entirety in this disclosure.

According to the invention, a foot powder includes boric acid powder and sublimed sulfur powder. In a number of embodiments, the foot powder includes about 40% to about 60% by weight of boric acid powder and about 40% to about 60% by weight of sublimed sulfur powder. In other embodiments, the ratio of boric acid powder to sublimed sulfur powder is about 1:1, that is, about 50% by weight of boric acid powder and about 50% by weight of sublimed sulfur powder.

In a number of embodiments, the foot powder includes only boric acid powder and sublimed sulfur powder with no additional ingredients. These embodiments enjoy the benefit of ease of production and low cost. In addition, the risk of allergic reaction that may have occurred with additional ingredients is eliminated.

The foot powders of the invention are effective in reducing or eliminating foot odor and wetness. For example, to treat foot odor, the foot powder may be applied topically to feet. In addition, as a regular regime, the feet may be washed and dried prior to applying the foot powder. The washing, drying, and applying steps may be performed on a daily basis. This daily regime may continue for an initial period, for example, two weeks or a month, depending upon the severity of odor. After the initial period, the washing, drying, and applying steps may be at a regular interval, for example, every other day, every three days, twice a week, etc., to control the odor. For treating foot wetness, the foot powder may be applied topically to the feet.

EXAMPLE

The following example further describes a specific embodiment within the scope of the present invention. In the following example, all ingredients are listed at an active level. The examples are given solely for the purpose of illustration and are not to be construed as limitations of the present invention, as many variations thereof are possible without departing from the spirit and scope of the invention.

A foot powder includes 50% by weight of boric acid powder and 50% by weight of sublimed sulfur powder. A commercial source of boric acid powder and sublimed sulfur powder in Spectrum Chemicals & Laboratory Products of 14422 South San Pedro Street, Gardena, Calif. 90248 (www.spectrumchemical.com). Commercial boric acid powder ($H_3BO_3$) generally includes a minimum of 99.5% boric acid, with the remainder including incidental chemicals. Commercial sublimed sulfur powder (S) generally includes a minimum of 99.5% of sulfur, with the reminder including incidental chemicals.

What is claimed is:

1. A foot powder consisting of:
   about 40% to about 60% by weight of boric acid powder; and
   about 40% to about 60% by weight of sublimed sulfur powder.

2. The foot powder of claim 1 wherein the ratio of boric acid powder to sublimed sulfur powder is about 1:1.

3. A method for treating foot odor, the method comprising:
   applying topically to feet a foot powder consisting of:
      about 40% to about 60% by weight of boric acid powder; and
      about 40% to about 60% by weight of sublimed sulfur powder.

4. The method of claim 3 further comprising prior to the applying step:
   washing the feet; and
   drying the feet.

5. The method of claim 4 further comprising:
   performing the washing, drying, and applying steps daily.

6. The method of claim 5 further comprising:
   repeating the performing step for an initial period.

7. The method of claim 6 wherein the initial period is about two weeks.

8. The method of claim 6 further comprising:
   performing the washing, drying, and applying steps at a regular interval after the initial period.

9. The method of claim 8 wherein the regular interval is about three days.

* * * * *